US00PP11313P

United States Patent [19]

Thomas

[11] Patent Number: Plant 11,313

[45] Date of Patent: Mar. 28, 2000

[54] YELLOW RASPBERRY PLANT NAMED 'KIWIGOLD'

[76] Inventor: Christopher Thomas, 64 Horrell Road, RD4, Morrinsville, New Zealand

[21] Appl. No.: 08/835,739

[22] Filed: Apr. 10, 1997

Related U.S. Application Data

[63] Continuation of application No. 08/569,888, Dec. 8, 1995, abandoned.

[51] Int. Cl.[7] ..... A01H 5/00

[52] U.S. Cl. ..... Plt./204

[58] Field of Search ..... Plt./46.2, 203, Plt./204

[56] References Cited

U.S. PATENT DOCUMENTS

P.P. 7,625 8/1991 Dixon ..... Plt./46.2

*Primary Examiner*—Howard J. Locker

[57] ABSTRACT

A new and unique raspberry 'Kiwigold' that has well-formed fruit of yellow color when ripe.

6 Drawing Sheets

This application is a continuation of application Ser. No. 08/569,888, filed Dec. 8, 1995, (abandoned).

BACKGROUND OF THE INVENTION

The present invention relates to a new and distinct asexually—reproduced variety of fall-bearing yellow raspberry, *Rubus idaeus,* known as 'Kiwigold' which is exceptional for its cohesive, well-formed fruit of yellow color when ripe.

ORIGIN

This new cultivar was discovered by Chris Thomas, on his farm on Horrell Road, Morrinsville, New Zealand. The original plant was a sport found within a commercial planting of 'Heritage' in March 1985 and was a naturally occurring whole plant mutation. The 'Heritage' crop was planted in August 1983 with dormant rooted canes taken from a nearby commercial planting. No other yellow fruiting plants had been seen in this field which was removed in 1987.

PROPAGATION

The original cane was marked and dug out when dormant to be planted in the home garden for observation. The next summer (1986) it produced many suckers and some of these fruited and appeared true to type of the original. Subsequently, suckers and the mother cane were planted in another area of the garden, isolated from 'Heritage' for multiplication.

In July 1988, enough planting material was available to plant out a cropping row and subsequently the area planted has been expanded to the present 2 acres. Plants are also being established for testing in the USA (Massachusetts) area, Scotland and England.

DESCRIPTION OF THE INVENTION

Figure 8:
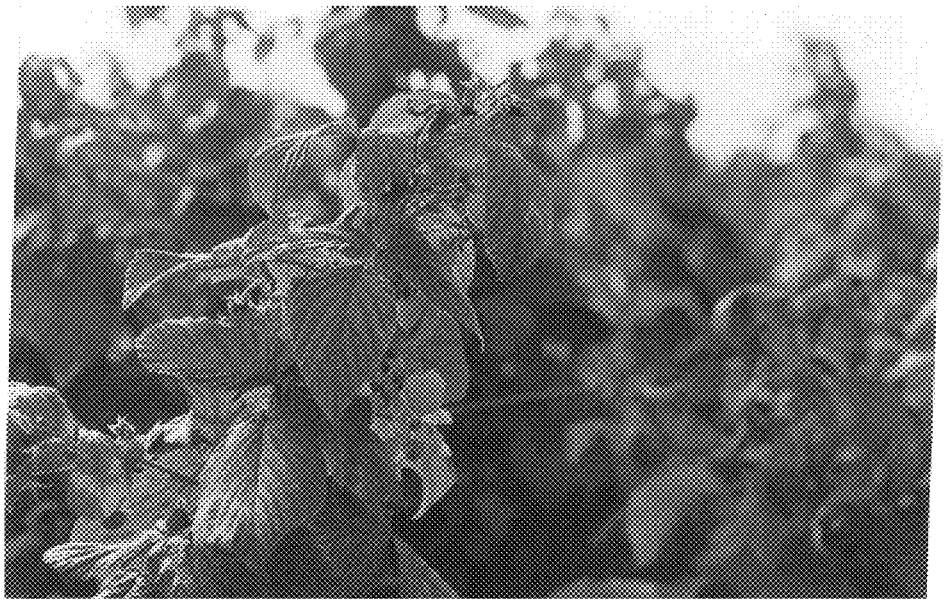
FIG. 8 shows the top portion of the growing plant and the yellow fruit.
Figure 9:
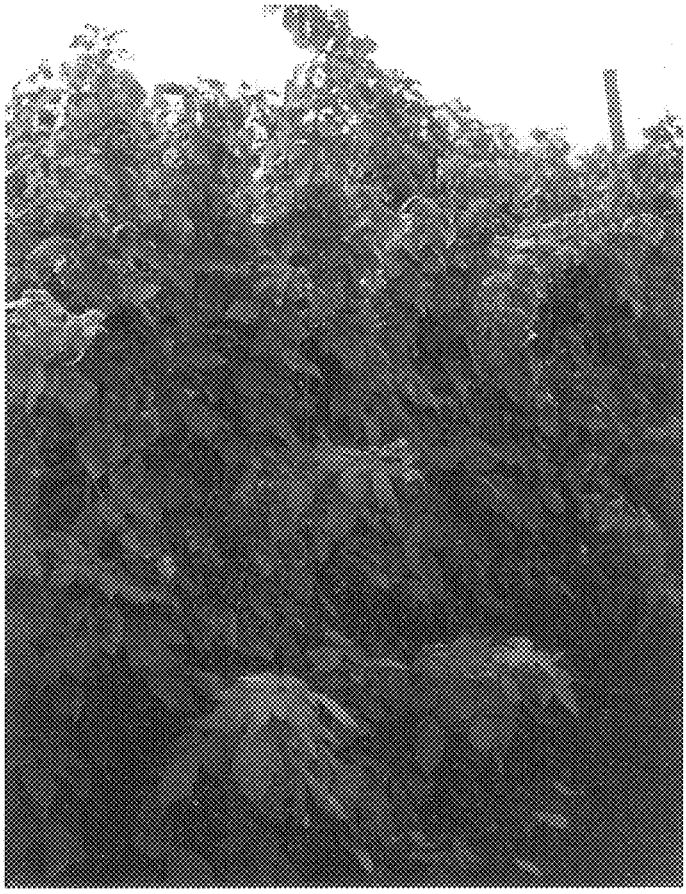
FIG. 9 shows a full view of the growing plant in fruit production.
Figure 10:
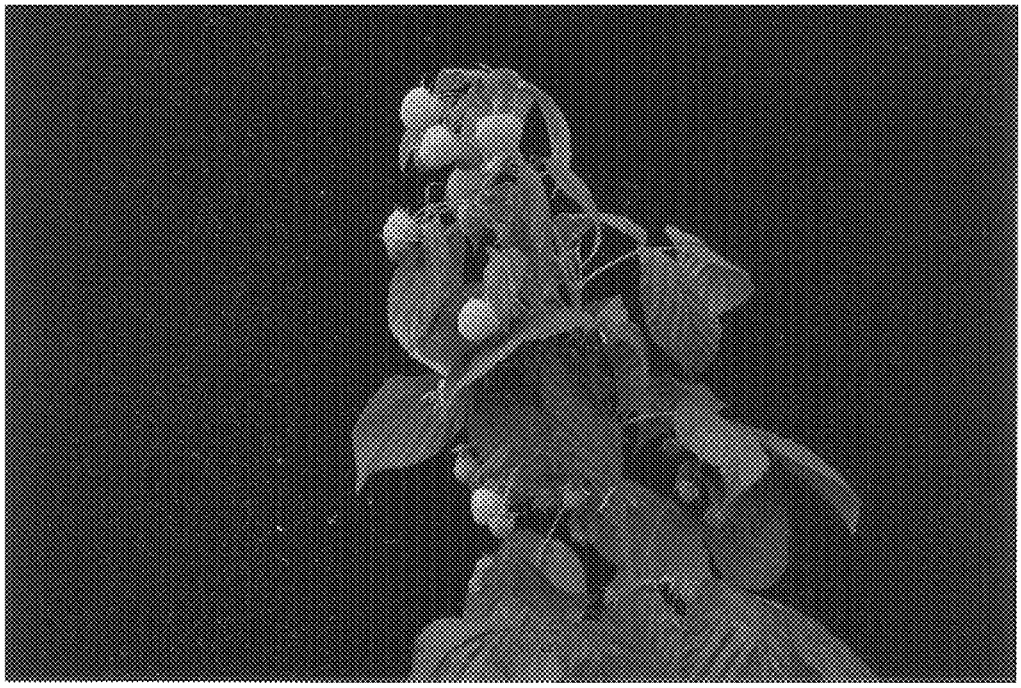
FIG. 10 shows a view of the growing point of the cane in fruit production.

A yellow raspberry plant 'Kiwigold' (FIGS. 8, 9 & 10) produces primocane fruit, which are more yellow when ripe than 'Graton Gold' which is sold under the trademark "Goldie" and is the subject of U.S. Plant Pat. No. 7,625. Growth habit and flowering characteristics are similar, as are fruiting season and overall yield. Berries are slightly smaller than 'Heritage' with similar flavor.

Figure 1:
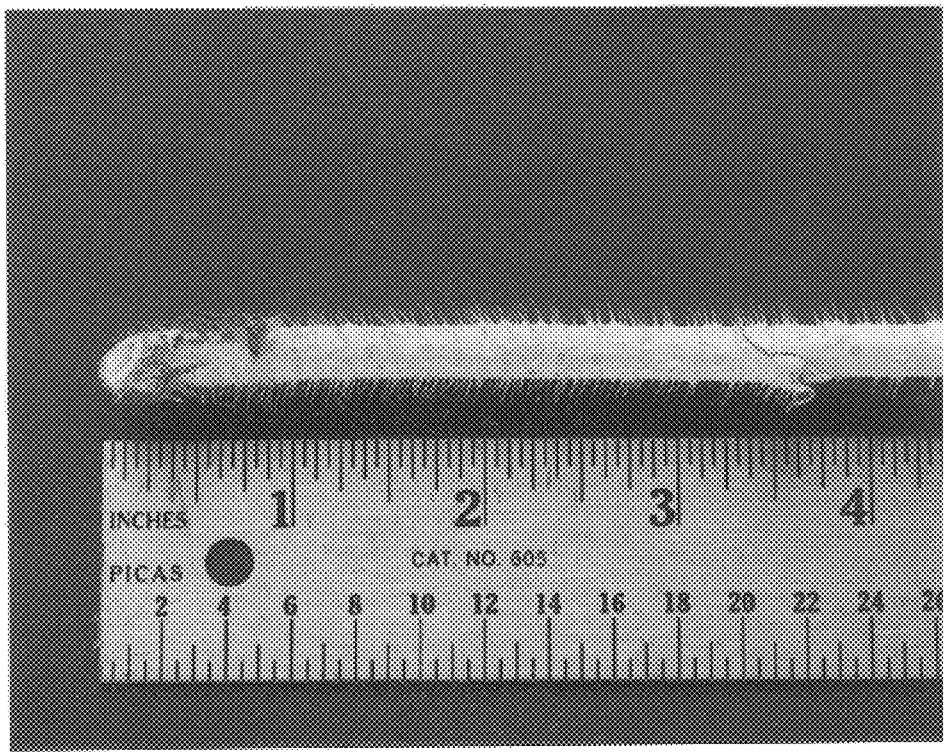
FIG. 1. shows the base of the 'Kiwigold' cane, showing thickly arranged fine spines. The spines are attached perpendicular and all green in color.
Figure 4:
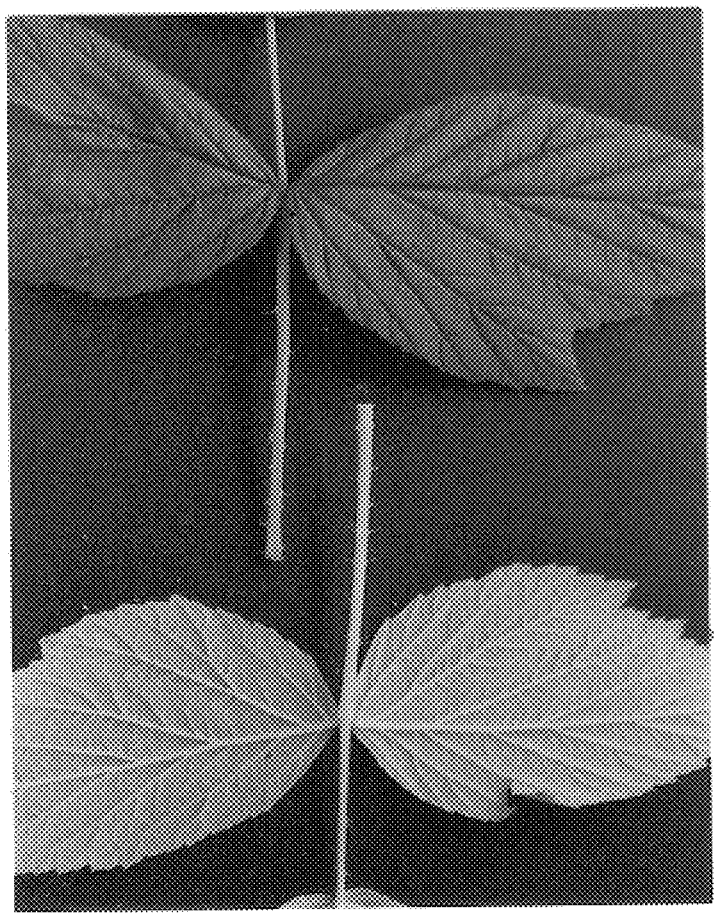
FIG. 4 shows a closer magnification of the vein structure of both the upper and lower side of the leaf and shows spine placement along the petiole.
Figure 5:
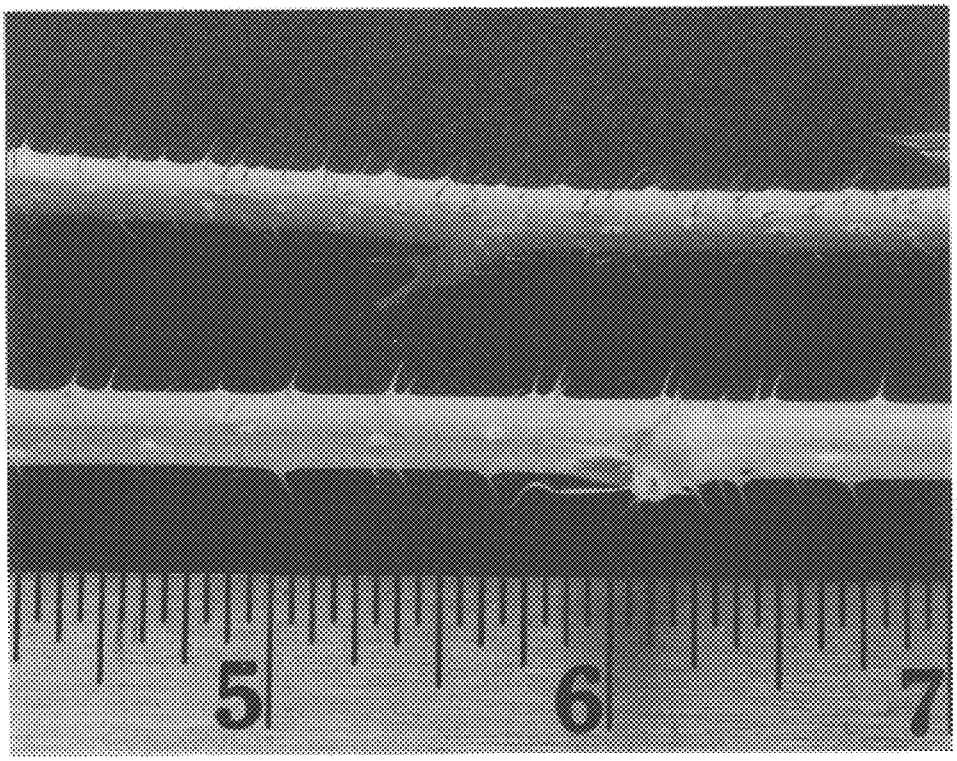
FIG. 5 shows a comparison between the stem of the 'Kiwigold' (lower cane) and 'Graton Gold' (U.S. Plant Pat. No. 7,625) (upper cane). The 'Graton Gold' spines have reddish-brown cast, are more numerous, shorter, more stout and are reflexed downward as compared to 'Kiwigold'.
Figure 6:
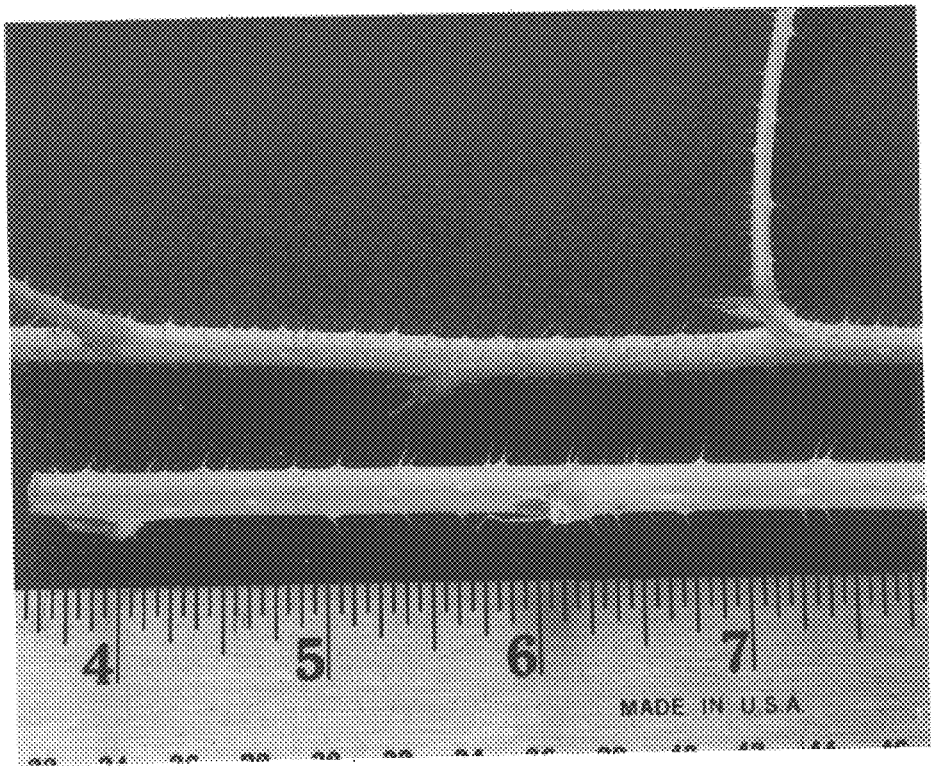
FIG. 6 shows a comparison between the stem of the 'Kiwigold' (lower cane) and 'Graton Gold' (upper cane). The 'Graton Gold' spines have reddish-brown cast, are more numerous, shorter, more stout and are reflexed downward as compared to 'Kiwigold', but in addition shows the more numerous placement of the spines on the petiole as compared to the petiole of 'Kiwigold' in FIG. 2.

The vegetative characteristics of 'Kiwigold' are similar to 'Graton Gold'.'Kiwigold' and 'Graton Gold' sucker moderately on fertile soil very similar to 'Heritage'. Variation in numbers of suckers produced and the caliper of individual suckers vary according to soil type and fertility. In a nursery production, a standard ratio of suckers produced per mother plant is 30:1 or 13 suckers per foot of row. Although both 'Kiwigold' and 'Graton Gold' have green primocanes, those of 'Kiwigold' are true green and those of 'Graton Gold' have a reddish-brown cast, especially towards the base (FIGS. 5 & 6). Spines are distributed uniformly along the canes and back of the leaf petioles (FIG. 4). The spines on 'Kiwigold' are attached perpendicular to the stem, are all green in color in natural light, and slightly longer and more fine. To the extent the spines of 'Kiwigold' appear to have a yellow cast in some figures herein, the color reflects the light source used to make the photos of the figures. The spines of 'Graton Gold' are shorter and more stout, are reflexed downward and have a reddish-brown cast especially on the top of the cane and along the back of the leaf petioles (FIGS. 5 & 6). Spines become more numerous and thickly arranged at the base of the primocane (FIG. 1) on both varieties, but attachment and size remain true to variety as described above (FIGS. 1 & 2).

Figure 2:
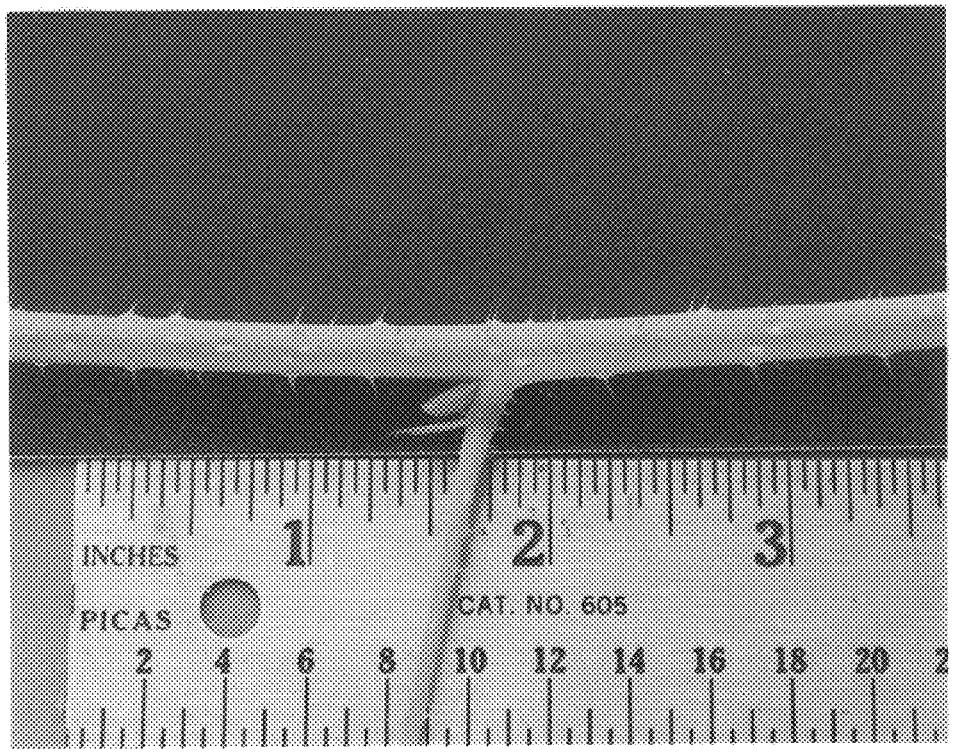
FIG. 2 shows the spine location mid-stem, attached perpendicular and green in color and also shows the location of spines on the petiole.
Figure 3:
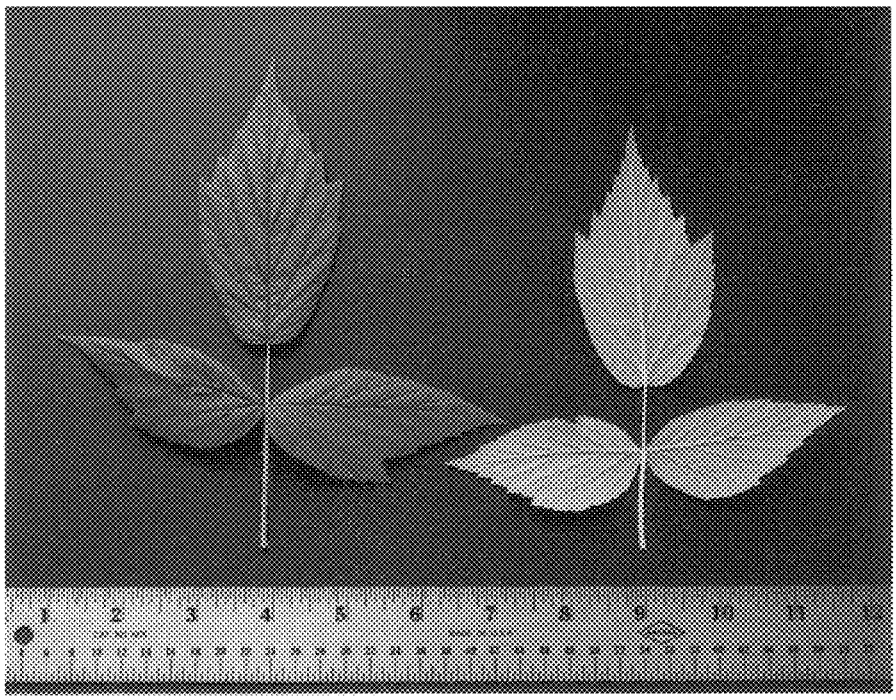
FIG. 3 shows the vein structure on both the upper and lower sides of the leaf and shows the serrations on the leaf edge.

The upper surfaces of leaves of both varieties are green at the base and yellow green towards the tip. The upper surfaces of lower leaves on both varieties have a predominant "thumb", similar to the 'Heritage' variety. The lower surfaces of the leaves of 'Kiwigold', 'Graton Gold' and 'Heritage' are very similar, light pale green in color, and descriptive characteristics in FIG. 4, such as veining, represent the appearance very accurately. The leaf petioles are attached almost perpendicular to the stem and have spines along the back side (FIG. 2). The leaves have no hairs on the upper surface but do have a fine pubescence on the lower surface only along the veins (FIGS. 3 & 4).

The flowers of 'Kiwigold' are white with yellow anthers and have a short petal structure. The flowers of 'Kiwigold', 'Graton Gold' and 'Heritage' are very similar.

Figure 7:
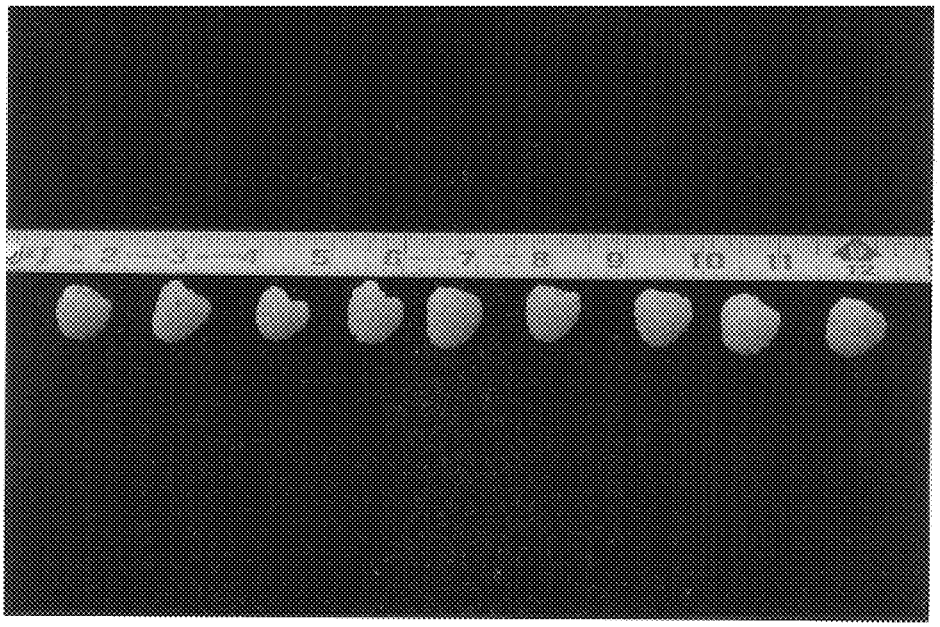
FIG. 7 shows the fruit to scale.
Figure 11:
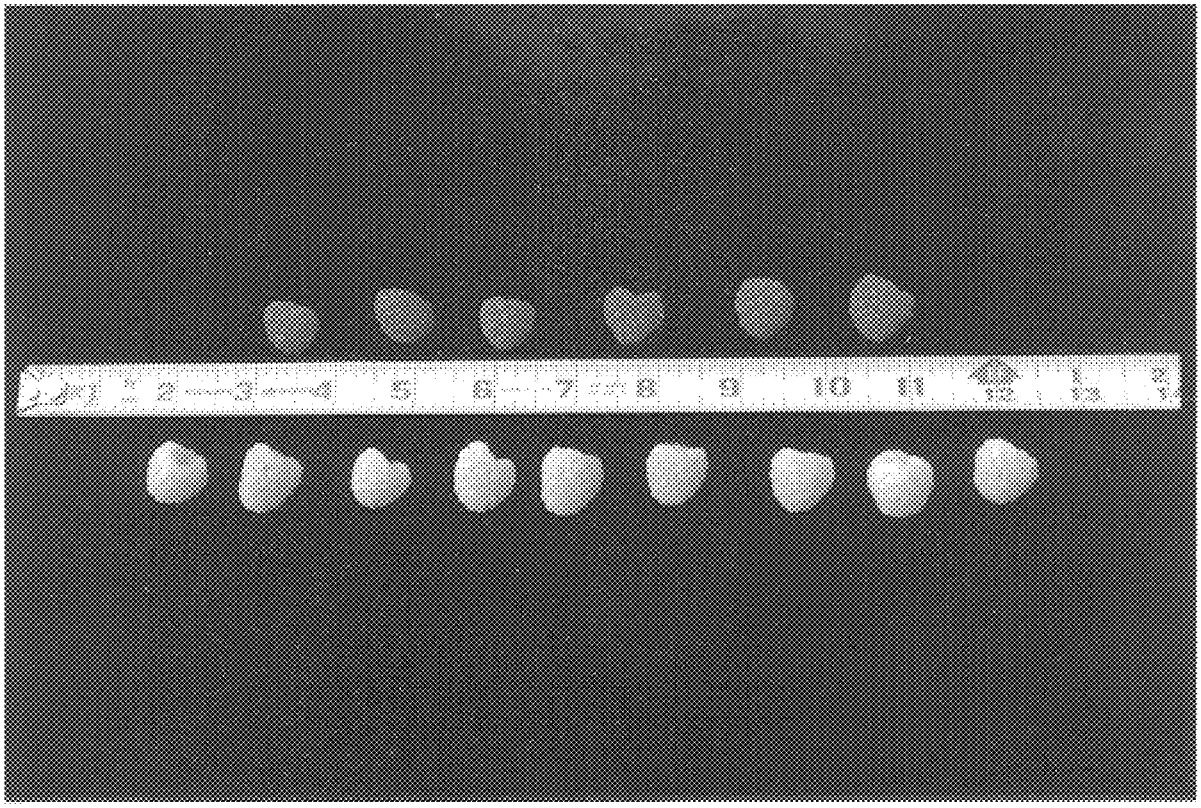
FIG. 11 shows the fruit of 'Kiwigold' (bottom—yellow fruit) in comparison to 'Heritage' (upper—red fruit).

The summer crop of fruit is relatively small. 'Kiwigold' may have a bit more value as it does not change color from yellow to orange as rapidly as 'Granton Gold' will during the warmer temperatures of July. The fall crop is sizable, approximately 3 tons per acre in New Zealand, very similar to 'Heritage'. Ripening season is similar between 'Granton Gold', 'Kiwigold' and 'Heritage'. In Massachusetts, 'Kiwigold' ripens at the same time as 'Graton Gold' and 'Heritage'. The ripening date changes according to environmental differences of each growing season. In Massachusetts, the first fruit of 'Kiwigold' was picked on Sep. 5, 1997 and on Aug. 21, 1998 . Fruit is cap shaped with uniform drupelet size and quite cohesive (FIG. 7 & 11). 'Kiwigold' fruit is slightly firmer and dryer than that of 'Granton Gold', and berry size is slightly smaller; 2.2 grams versus 2.35 grams on October 1st in Massachusetts. The fruit size of 'Kiwigold' is very comparable to the fruit size of 'Granton Gold' and the fruit size of 'Heritage'. In Massachusetts, on Oct. 1, 1998, the average width of fruit of 'Kiwigold' ranged from 11/16 inch to 14/16 inch and the average length of fruit of 'Kiwigold' ranged from 12/16 inch to 13/16 inch. Color of 'Kiwigold' fruit is more yellow than that of 'Graton Gold', changing to a light orange-red with fully ripe, verses a dark orange-red on 'Graton Gold'. The first year wood or primocanes of 'Kiwigold' produces about 80 percent of the total crop. The fruit of the first year wood is 20% larger than the fruit of the second year wood. The second year wood produces about 20% of the crop. These values for 'Kiwigold' for first year wood, fruit on the first year wood, and second year wood are similar for 'Graton Gold' and 'Heritage'. 'Kiwigold' has slightly more acidity than 'Graton Gold', but less acidity than 'Heritage'. Flavor 'Kiwigold' fruit is less sweet than 'Graton Gold' yet sweeter than 'Heritage'. The eating quality of 'Kiwigold' is above average for raspberries. Although there is a slight difference in eating quality for 'Kiwigold' compared to 'Heritage', in blindfold tests, the vast majority of people would not detect a difference.

'Kiwigold' appears to be tolerant to powdery mildew, similar to 'Heritage' and also has similar susceptibility to phytophthora root rot.

'Kiwigold' can be distinguished from 'Graton Gold' in the following ways. The plant appears to be completely devoid of anthocyanin making stem and leaf color all true green, where as 'Graton Gold' has a reddish brown cast to portions of the stem, leaves, and spines. The spines of 'Kiwigold' are attached perpendicular, are longer, finer and true green all along the cane, whereas 'Graton Gold' has shorter, stouter spines that definitely point downward and have a reddish brown cast especially at the primocane tip and backs of leaf petioles. The fruit of 'Kiwigold' is more yellow than 'Graton Gold' and slightly smaller.

According to The Royal Horticultural Society (R.H.S.) color chart, 'Kiwigold' colors can be characterized as shown below. It must be kept in mind that coloration in plants is highly dependant upon environmental conditions such as light, temperature, stress, etc. Therefore, these colors can only be considered approximations:

1. Stem color (shaded): Yellow-Green 146B—146C.
2. Stem color (full sun): Yellow-Green 145B.
3. Leaf color (mature): Green 137A.
4. Leaf color (primocane tip): Yellow-Green 144A.
5. Fruit color (just ripe): Yellow-Orange 20B.
6. Fruit color (fall-off ripe): Orange-Red 30A—30B.

According to the Munsell Color Chart for Plant Tissues, $2^{nd}$ edition, revised 1997, the color for the underside of a 'Kiwigold' leaf is 7.5 GY, 6/4.

What is claimed:

1. A new and distinct raspberry cultivar as herein described and illustrated.

* * * * *